United States Patent
Wall et al.

(10) Patent No.: US 7,481,830 B2
(45) Date of Patent: *Jan. 27, 2009

(54) SPINAL CORRECTION SYSTEM

(75) Inventors: Eric J. Wall, Cincinnati, OH (US); Donita I. Bylski-Austrow, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 591 days.

This patent is subject to a terminal disclaimer.

(21) Appl. No.: 10/862,660

(22) Filed: Jun. 7, 2004

(65) Prior Publication Data

US 2004/0220569 A1 Nov. 4, 2004

Related U.S. Application Data

(63) Continuation of application No. 10/030,440, filed as application No. PCT/US00/18491 on Jul. 6, 2000, now Pat. No. 6,746,450.

(60) Provisional application No. 60/142,707, filed on Jul. 7, 1999.

(51) Int. Cl.
*A61B 17/80* (2006.01)

(52) U.S. Cl. .......................... 606/297; 606/75; 606/286

(58) Field of Classification Search ............. 606/69–71, 606/72, 75
See application file for complete search history.

(56) References Cited

U.S. PATENT DOCUMENTS

| | | | |
|---|---|---|---|
| 3,693,616 A | 9/1972 | Roaf et al. | |
| 3,862,631 A | 1/1975 | Austin | |
| 4,041,939 A | 8/1977 | Hall | |
| 4,047,523 A | 9/1977 | Hall | |
| 4,047,524 A | 9/1977 | Hall | |
| 4,078,559 A | 3/1978 | Nissinen | |
| 4,401,112 A | 8/1983 | Rezaian | |
| 4,403,606 A * | 9/1983 | Woo et al. | 606/70 |
| 4,434,796 A | 3/1984 | Karapetian et al. | |
| 4,454,875 A * | 6/1984 | Pratt et al. | 606/75 |

(Continued)

FOREIGN PATENT DOCUMENTS

EP 0 026 970 A1 4/1981

(Continued)

OTHER PUBLICATIONS

"Control of Bone Growth by Epiphyseal Stapling: A Preliminary Report," by Walter P. Blount, MD et al., The Journal of Bone and Joint Surgery, vol. 31-A, No. 3, Jul. 1949.

(Continued)

*Primary Examiner*—Eduardo C Robert
*Assistant Examiner*—Jerry Cumberledge
(74) *Attorney, Agent, or Firm*—Baker & Daniels LLP (57) ABSTRACT

A spinal correction system for the correction or arrest of scoliosis or spinal deformity in immature spines includes a bridge member, a pair of spaced apart barbed legs extending substantially perpendicularly therefrom, and a fastener retaining portion extending substantially longitudinally from each end of the bridge member. The fastener retaining portions are adapted to lie in adjoining relationship when two or more spinal correction systems are arranged in end-to-end abutting relationship. The spinal correction system is intended to correct or arrest scoliosis in a growing spine by spanning the endplate growth centers of adjacent vertebrae, on the convex side of the malformed spine, to retard growth of that side of the spine while permitting unrestrained growth of the concave side of the spine.

32 Claims, 10 Drawing Sheets

U.S. PATENT DOCUMENTS

| | | | |
|---|---|---|---|
| 4,462,395 | A | 7/1984 | Johnson |
| 4,503,848 | A * | 3/1985 | Caspar et al. ................. 606/69 |
| 4,570,618 | A | 2/1986 | Wu |
| 4,570,623 | A | 2/1986 | Ellison et al. |
| 4,573,454 | A | 3/1986 | Hoffman |
| 4,592,346 | A * | 6/1986 | Jurgutis ....................... 606/75 |
| 4,599,086 | A | 7/1986 | Doty |
| 4,651,724 | A | 3/1987 | Berentey et al. |
| 4,686,970 | A | 8/1987 | Dove et al. |
| 4,743,260 | A | 5/1988 | Burton |
| 4,776,851 | A | 10/1988 | Bruchman et al. |
| 4,793,335 | A * | 12/1988 | Frey et al. ................ 623/13.14 |
| 4,841,960 | A | 6/1989 | Garner |
| 4,848,328 | A | 7/1989 | Laboureau et al. |
| 4,870,957 | A | 10/1989 | Goble et al. |
| 4,913,144 | A | 4/1990 | Del Medico |
| 4,943,292 | A * | 7/1990 | Foux ........................... 606/70 |
| 4,955,910 | A | 9/1990 | Bolesky |
| 4,960,420 | A * | 10/1990 | Goble et al. ................. 606/72 |
| 4,966,600 | A | 10/1990 | Songer et al. |
| 4,998,936 | A | 3/1991 | Mehdian |
| 5,002,574 | A | 3/1991 | May et al. |
| 5,011,484 | A | 4/1991 | Breard |
| 5,030,220 | A | 7/1991 | Howland |
| D320,081 | S | 9/1991 | Johnson |
| 5,053,038 | A | 10/1991 | Sheehan |
| 5,092,866 | A | 3/1992 | Breard et al. |
| 5,092,868 | A | 3/1992 | Mehdian |
| 5,108,395 | A | 4/1992 | Laurain et al. |
| 5,116,340 | A | 5/1992 | Songer et al. |
| 5,147,361 | A | 9/1992 | Ojima et al. |
| 5,180,393 | A | 1/1993 | Commarmond |
| 5,199,146 | A | 4/1993 | Grover et al. |
| D340,284 | S | 10/1993 | Johnson |
| 5,261,910 | A | 11/1993 | Warden et al. |
| 5,306,301 | A | 4/1994 | Graf et al. |
| 5,318,566 | A | 6/1994 | Miller |
| 5,324,290 | A | 6/1994 | Zdeblick et al. |
| 5,352,229 | A * | 10/1994 | Goble et al. ................. 606/75 |
| 5,387,213 | A | 2/1995 | Breard et al. |
| 5,395,372 | A | 3/1995 | Holt et al. |
| 5,395,374 | A | 3/1995 | Miller et al. |
| 5,405,391 | A | 4/1995 | Hednerson et al. |
| 5,415,658 | A | 5/1995 | Kilpela et al. |
| 5,415,661 | A | 5/1995 | Holmes |
| 5,417,690 | A | 5/1995 | Sennett et al. |
| 5,423,820 | A | 6/1995 | Miller et al. |
| 5,425,767 | A | 6/1995 | Steininger et al. |
| 5,449,359 | A | 9/1995 | Groiso |
| 5,454,814 | A * | 10/1995 | Comte ......................... 606/75 |
| 5,456,722 | A | 10/1995 | McLeod et al. |
| D364,462 | S | 11/1995 | Michelson |
| 5,476,465 | A | 12/1995 | Preissman |
| 5,496,318 | A | 3/1996 | Howland et al. |
| 5,536,270 | A | 7/1996 | Songer et al. |
| 5,540,698 | A | 7/1996 | Preissman |
| 5,540,703 | A | 7/1996 | Barker, Jr. et al. |
| 5,545,168 | A | 8/1996 | Burke |
| 5,569,253 | A | 10/1996 | Farris et al. |
| 5,603,713 | A | 2/1997 | Aust et al. |
| D378,409 | S | 3/1997 | Michelson |
| 5,607,425 | A | 3/1997 | Rogozinski |
| 5,609,634 | A | 3/1997 | Voydeville |
| 5,620,443 | A | 4/1997 | Gertzbein et al. |
| 5,649,927 | A | 7/1997 | Kilpela et al. |
| 5,653,711 | A | 8/1997 | Hayano et al. |
| 5,662,655 | A * | 9/1997 | Laboureau et al. ............ 606/75 |
| 5,669,917 | A | 9/1997 | Sauer et al. |
| 5,693,046 | A | 12/1997 | Songer et al. |
| 5,702,395 | A | 12/1997 | Hopf |
| 5,702,399 | A | 12/1997 | Kilpela et al. |
| 5,707,395 | A | 1/1998 | Li |
| 5,713,900 | A * | 2/1998 | Benzel et al. ................. 606/61 |
| 5,720,747 | A | 2/1998 | Burke |
| 5,725,582 | A | 3/1998 | Bevan et al. |
| 5,741,260 | A | 4/1998 | Songer et al. |
| 5,908,421 | A | 6/1999 | Beger |
| 6,066,140 | A | 5/2000 | Gertzbein et al. |
| 6,228,085 | B1 | 5/2001 | Theken et al. |
| 6,231,610 | B1 | 5/2001 | Geisler |
| 6,235,059 | B1 * | 5/2001 | Benezech et al. ......... 623/17.16 |
| 6,296,643 | B1 | 10/2001 | Hopf et al. |
| 6,299,613 | B1 | 10/2001 | Ogilvie et al. |
| 6,309,393 | B1 | 10/2001 | Tepic et al. |
| 6,325,805 | B1 | 12/2001 | Ogilvie et al. |
| 6,336,928 | B1 | 1/2002 | Guerin et al. |
| 6,436,099 | B1 | 8/2002 | Drewry et al. |
| 6,517,564 | B1 * | 2/2003 | Grafton et al. ............... 606/213 |
| 6,551,320 | B2 | 4/2003 | Lieberman |
| 6,616,669 | B2 | 9/2003 | Ogilvie et al. |
| 6,623,484 | B2 | 9/2003 | Betz et al. |

FOREIGN PATENT DOCUMENTS

| | | |
|---|---|---|
| EP | 0 478 470 A1 | 1/1992 |
| EP | 0 545 830 A1 | 6/1993 |
| EP | 0 552 109 A | 7/1993 |
| EP | 0 625 336 A2 | 11/1994 |
| FR | 2 709 410 | 3/1995 |
| JP | 63-65060 | 4/1988 |
| JP | 3-75717 U | 7/1991 |
| JP | 7-79998 | 3/1995 |
| JP | 8-229052 | 9/1996 |
| JP | WO 98/17189 | 4/1998 |
| JP | WO 98/48718 | 11/1998 |
| WO | WO 91/16018 | 10/1991 |
| WO | WO 94/01057 | 1/1994 |
| WO | WO 94/26192 | 11/1994 |
| WO | WO 98/51226 | 11/1998 |

OTHER PUBLICATIONS

"An Operation for Stapling Vertebral Bodies in Congenital Scoliosis," by A.D. Smith et al., The Journal of Bone and Joint Surgery, vol. 36-A, No. 2, pp. 342-348, Apr. 1954.

"Endoscopic Discectomy Increases Thoracic Spine Flexibilty as Effectively as Open Discectomy: A Mechanical Study in a Porcine Model," by Eric J. Wall, et al., Spine vol. 23(1), pp. 9-15, Jan. 1, 1998.

"The Prediction of Curve Progression in Untreated Idiopathic Scoliosis During Growth," by John E. Lonstein et al., The Journal of Bone and Joint Surgery, vol. 66-A, No. 7, Sep. 1984.

A Mature Look at Epiphyseal Stapling, Walter P. Bount, MD, Clinical Orthopaedics and Related Research, No. 77, Jun. 1971.

Convex Growth Arrest for Progressive Congenital Scoliosis Due to Hemivertebrae, Robert B. Winter, MD, et al., Journal of Pediatric Orthopaedics, vol. 8, No. 6, 1988.

Influence of Epiphyses on the Regulation of Bone Growth, E.C.B. Hall-Craggs, Nature, vol. 221, Mar. 29, 1969.

Paper: "Endoscopic Nonfusion Spinal Hemiepiphysiodesis: Preliminary studies in a porcine model," by D. I. Bylski-Austrow et al., Jan. 1999.

"An Analysis of the Effect of the Zielke Operation on S-shaped Curves in Idiopathic Scoliosis: A Follow-up Study Revealing Some Skeletal and Soft Tissue Factors Involved in Curve Progression," by A.S. Wojcik, MD et al., Spine, vol. 15, No. 8, 1990.

"An Operation for Stapling Vertebral Bodies in Congenital Scoliosis," by Alan DeForest Smith, MD et al., The Journal of Bone and Joint Surgery, vol. 36-A, No. 2, Apr. 1954.

"Attempted Treatment of Scoliosis by Unilateral Vertebral Epiphyseal Arrest," by H.R. McCarroll, MD et al., The Journal of Bone and Joint Surgery, vol. 42-A, No. 6, Sep. 1960.

"CDH: preliminary report on a new anterior spinal instrumentation," by C. Hopf et al., European Spine Journal, Spring 1994.

"Comparison Between Single-Screw and Triangulated, Double-Screw Fixation in Anterior Spine Surgery: A Biomechanical Test," by Michael Ogon, MD et al., Spine, vol. 21, No. 23, 1996.

"Control of Bone Growth by Epiphyseal Stapling: A Preliminary Report," by Walter P. Bount, M et al., Clinical Orthopaedics and Related Research, No. 77, Jun. 1971.

"Convex Anterior and Posterior Hemiarthrodesis and Hemiepiphysiodesis in Young Children with Progressive Congenital Scoliosis ," by Robert B. Winter, Journal of Pediatric Orthopaedics, vol. 1, No. 4, 1981.

"Growth Arrest for Progressive Scoliosis: Combined Anterior and Posterior Fusion of the Convexity," by Terry Andrew et al., The Journal of Bone and Joint Surgery, vol. 67-B, No. 2, Mar. 1985.

"Growth Modification in the Treatment of Scoliosis," by Harry Piggot, FRCS, Orthopedics, vol. 10, No. 6, Jun. 1987.

"Histologic Arrangements from Biopsies Plates of Children Before and After Stapling." by Charles Weer Goff, MD, American Journal of Orthopedics, May 1967.

"Mechanical Modulation of Vertebral Body Growth; Implications for Scoliosis Progression," by Ian A.F. Stokes, Ph.D. et al., Spine, vol. 21, No. 10, 1996.

"Operative Treatment of Scoliosis With Cotrel-Dubousset-Hopf Instrumentation: New Anterior Spinal Device," by Christopher G. Hopf et al., Spine, vol. 22, No. 6, 1997.

"Progression of Vertebral Wedging in an Asymmetrically Loaded Rat Tail Model," by Peter L. Mente, Ph.D. et al., Spine, vol. 22, No. 12, 1997.

"Retardation of Bone Growth by a Wire Loop," by S.L. Haas, MD, The Journal of Bone and Joint Surgery, vol. 27, No. 1, Jan. 1945.

"The Cure of Experimental Scoliosis by Directed Growth Control," by I. William Nachlas, MD et al., The Journal of Bone and Joint Surgery, vol. 33-A, No. 1, 1951.

"The Effect of Epiphysial Stapling on Grwoth in Length of the Rabbit's Tibia and Femur," by E.C.B. Hall-Craggs et al., The Journal of Bone and Joint Surgery, vol. 51, No. 2, May 1969.

"The Effects of Mechanical Forces on Bones and Joints: Experimental Study on the Rat Tail," by Ugo E. Pazzaglia et al., The Journal of Bone and Joint Surgery, vol. 79-B, No. 6, Nov. 1997.

"The Treatment of Progressive Scoliosis by Unilateral Growth-Arrest," by Robert Roaf, The Journal of Bone and Joint Surgery, vol. 45-B, No. 4, Nov. 1963.

"Transpedicular Convex Anterior Hemiepiphysiodesis and Posterior Arthrodesis for Progressive Congenital Scoliosis," by Andrew G. King, MB, et al., Spine, vol. 17, No. 8S, 1992.

"Vertebral Growth and Its Mechanical Control," by Robert Roaf, The Journal of Bone and Joint Surgery, vol. 42-B, No. 1, Feb. 1960.

* cited by examiner

SPINAL CORRECTION SYSTEM

CROSS-REFERENCE TO RELATED APPLICATIONS

This application is a continuation of U.S. patent application Ser. No. 10/030,440, filed Jan. 7, 2002, now U.S. Pat. No. 6,746,450 which is the national phase under 35 U.S.C. § 371 of PCT International Application No. PCT/US00/18491, having a filing date of Jul. 6, 2000, which claims the benefit of U.S. Provisional Patent Application Ser. No. 60/142,707, filed Jul. 7, 1999, all of which are expressly incorporated by reference herein.

BACKGROUND OF THE INVENTION

This invention relates to devices for use in the correction, arresting or slowing of abnormal curvature of the spine, including scoliosis, hyperlordosis and hypokyphosis.

Juvenile and adolescent scoliosis is a disorder of the growing spine in which a predominantly lateral curvature develops. Curves over 40° can require surgical correction due to the high risk of future progression during adulthood. One typical procedure, often called "posterior approach scoliosis surgery," is one of the most invasive human surgeries in orthopedics. During a typical three to eight hour procedure, a surgeon strips the strong posterior muscles off of the spine for bone exposure, then attaches two metal rods to the spine with hooks, wires, or screws. An alternative scoliosis approach is through the anterior chest via thoracotomy or thoracoscopy. After multi-level discectomy and fusion, large screws are placed across the vertebral bodies, and then the screws and vertebrae are compressed together by means of a vertical rod.

Staples are often used in orthopaedics to fix two bones or pieces of bone together, such as would be required for osteotomy (bone cutting), or fracture stabilization. Staples typically used for these purposes are disclosed in U.S. Pat. Nos. 4,434,796 by Karapetian; 3,862,621 to Austin; 4,841,960 to Garner; 4,848,328 to Laboureau et al.; 5,449,359 to Groiso; 5,053,038 to Sheehan; and 4,913,144 to Del Medico.

Orthopaedic staples are also used in the fixation of soft tissue to bone, such as tendon or shoulder tissue. Staples typically used for these purposes are described in U.S. Pat. Nos. 5,352,229 to Goble et al.; 4,462,395 to Johnson; 4,570,623 to Ellison et al.; 4,454,875 to Pratt et al.; D320,081 to Johnson; and D340,284 to Johnson.

In addition, several screws with a linkage plate or rod have been developed for anterior spine fixation and are described in U.S. Pat. Nos. 5,324,290 to Zdeblick et al.; and 4,041,939 to Hall.

Additional U.S. Patents disclose spine staples, for example U.S. Pat. Nos. 4,047,523 to Hall; 4,047,524 to Hall; 5,395,372 to Holt et al.; D378,409 to Michelson; and D364,462 to Michelson.

The inventors have developed a novel procedure for correcting scoliosis in children that takes advantage of future spine growth to correct the scoliosis. This procedure relies upon slowing spine epiphyseal growth on the convex side of the scoliosis curve with a novel hemiepiphyseal spinal correction system.

The novel procedure using the novel spinal correction system requires only one-fourth of the time necessary for conventional implantation techniques and may be performed using minimally invasive endoscopic procedures. In addition, the novel spinal correction system has an extremely low profile which reduces the risk of neurological complications.

This new procedure uses a novel system of staples and screws to provide anterior non-fusion (no bone graft) correction of scoliosis in children with significant growth remaining. The procedure can be performed entirely endoscopically in as little as one hour of surgical time. This procedure using the novel spinal staple avoids the complex rod-screw linkage of current anterior scoliosis corrective systems. It also holds the potential for making correction an outpatient procedure and minimizes blood loss during surgery.

Existing spinal implants do not take advantage of the hemiepiphysiodesis principle of altering spine growth and allowing for gradual correction through asymmetric growth. Prior art bone staples used to fix two bones or pieces of bone together, for example, are not designed to perform hemiepiphysiodesis, and are not designed or able to resist the forces of spinal motion and growth without significant splay. Orthopaedic staples used to fix soft tissue to bone are not designed to span two bones or two pieces of bone. Thus, such staples are inapplicable to the novel procedure for the correction of scoliosis in children.

The other staples mentioned above were not designed for spine hemiepiphysiodesis and are instead intended for other purposes. For example, U.S. Pat. No. 4,041,939 to Hall discloses small staples to stabilize a screw-bone interface and to prevent migration or plowing of a screw through a bone. Likewise, U.S. Pat. No. 4,047,524 to Hall discloses a spinal staple meant to stabilize the screw-bone interface of a screw and rod system. U.S. Pat. No. 4,047,523 to Hall discloses a surgical sacral anchor implant that is half of a staple blade affixed to a cable for the fixation of the lower end of the spine. U.S. Pat. No. 5,395,372 to Holt et al., is a spinal staple that holds a strut bone graft in place and is designed for use after vertebrectomy.

Thus, there exists a need for a spinal correction system that is small and designed to span vertebral endplate growth centers on either side of a disk.

SUMMARY OF THE INVENTION

The above noted concerns and needs are addressed by the novel spinal correction system including a spinal staple in accordance with the invention. The spinal staple includes a bridge member having a length sufficient to span the vertebral endplate growth centers on either side of a vertebral disk. A pair of spaced apart wedged-shaped legs extend downwardly from the end of the bridge member and are of such a length as to penetrate no more than about half way into the depth of a vertebra. Fastener retaining portions extend horizontally outward from the opposite ends of the bridge member and define passageways therethrough adapted to receive fasteners such as screws and the like. The fastener retaining portions are proportioned so that when two or more of the spinal staples of the invention are arranged in end-to-end adjoining relationship, the fastener retaining portions extending from the abutting ends lie side by side.

The legs of the staple are equipped with barbs to resist backing out or loosening of the staple after it has been affixed to a vertebra. In addition, the fastener retaining portions have barbs or projections extending from a lower surface thereof to promote fixation of the staple in a vertebra. Optionally, the staple may be provided with a threaded cannulated post extending upward from the upper surface of the bridge member to allow attachment of a threaded removable, cannulated impaction device. Further, additional surgical hardware may be conveniently affixed to the staple by means of the threaded post.

The invention will be further described and illustrated in conjunction with the following detailed description and appended drawings.

DETAILED DESCRIPTION OF THE DRAWINGS

Referring to FIGS. 1-6, a spinal staple 10 constructed in accordance with the invention is shown. The staple 10 includes a bridge member 12, a pair of spaced apart legs 14, a left fastener retaining portion 16, a right fastener retaining portion 18, and an attachment member, illustratively a threaded post 20. Although reference will be made throughout this description to terms implying direction such as left, right, front, back, upper and lower, these terms are used only for convenience in describing the staple 10 and should not be read as limiting the staple 10 to any particular orientation.

The bridge member 12 includes an upper surface 22, an opposed lower surface 24, a front side 26, an opposed back side 28, a left end 30 and an opposed right end 32. The upper surface 22 is substantially planar in a direction extending from the left end 30 to the right end 32, and is convex in a direction from the front side 26 to the back side 28, as may best be seen in FIG. 5 when the staple is viewed from one of the ends. The lower surface 24 is concave in a direction from the left end 30 to the right end 32 and from the front side 26 to the back side 28, as may best be seen in FIGS. 2 and 3. The bridge member 12 thus defines a pair of cooperating arches, a first arch extending between the left and right ends 30 and 32 and a second arch extending between the front and back sides 26 and 28.

Figure 1:
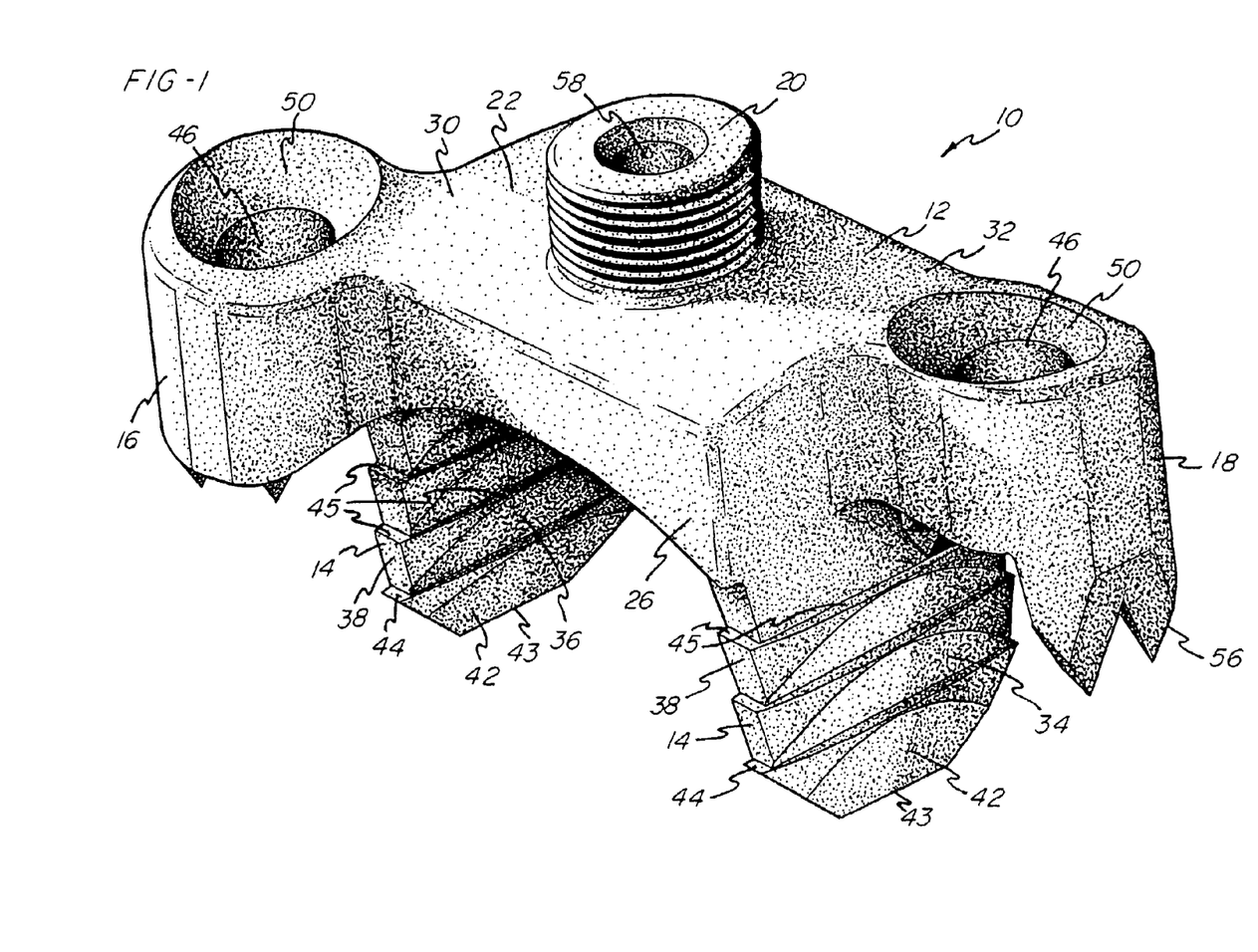
FIG. 1 is a perspective view of a spinal staple in accordance with the invention.
Figure 2:
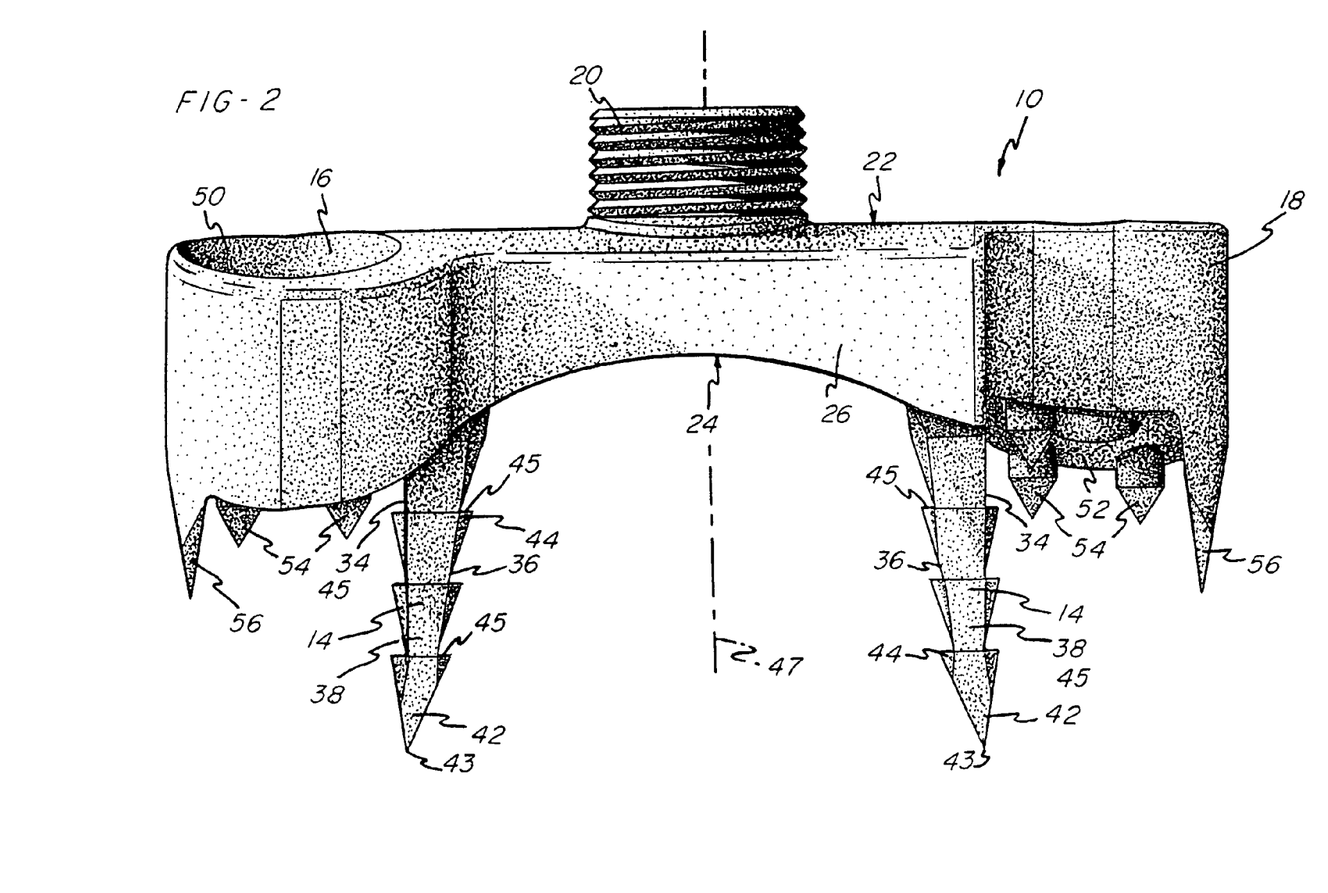
FIG. 2 is a front elevation view of the spinal staple of FIG. 1.
Figure 3:
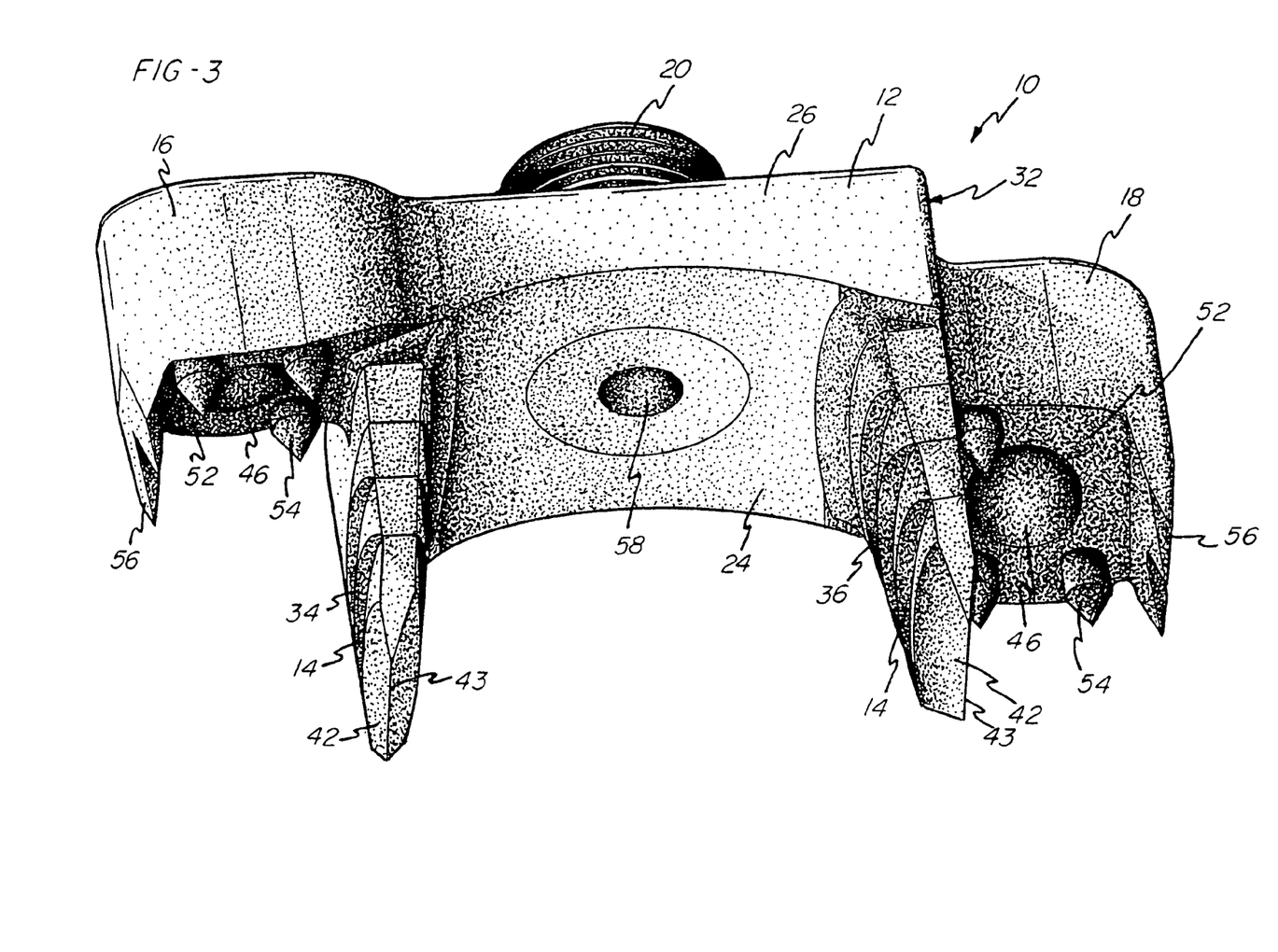
FIG. 3 is a perspective view of the spinal staple showing the underside of the staple.

The legs 14 extend downwardly from the lower surface 24 at the left and right ends 30, 32, and are substantially wedge-shaped. Each leg 14 has an outer surface 34, an opposed inner surface 36 such that the inner surfaces 36 are facing each other, a front surface 38, and an opposed back surface 40. Each of the legs 14 has a width as measured from the front surface 38 to the back surface 40, which is substantially equal to the width of the bridge member 12 as measured from the front side 26 to the back side 28. As shown in FIGS. 1-3, the width of each leg 14 is several times greater than the thickness of the respective leg 14, as measured from the outer surface 34 to the inner surface 36. The legs 14 narrow slightly from the front surface 38 to the back surface 40 toward their respective tips 42 which are sharply tapered to define a blade edge 43. Barbs 44 project outwardly from each of the outer, inner, front, and back surfaces 34, 36, 38 and 40, respectively.

Each barb 44 includes a retaining surface 45 facing generally away from the respective tip 42 and facing generally toward the bridge member 12. As such, the barbs 44 are adapted to inhibit withdrawal movement of the staple 10 once the staple 10 has been positioned in its fixation environment, such as a vertebra. The inner surface 36 of the legs 14 are preferably splayed, or angled, away from each other at an angle of about 10° as measured from a vertical plane 47 extending perpendicularly through the cross-section of the bridge member 12. The outer surfaces 34 of the legs 14 extend downwardly substantially perpendicular to the bridge member 12 and substantially parallel to the vertical plane 45.

Figure 6:
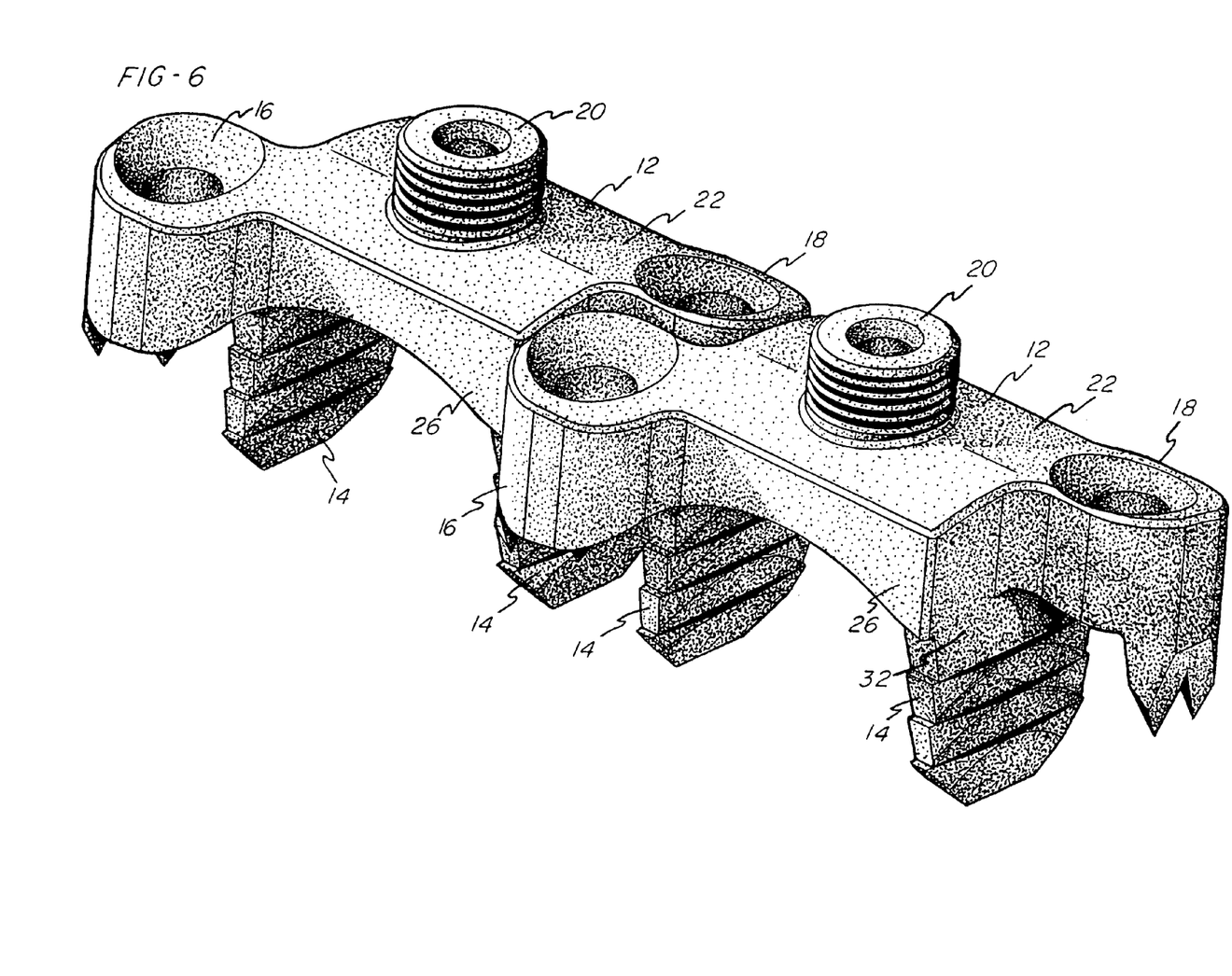
FIG. 6 is a perspective view of two of the spinal staples in accordance with the invention aligned in end-to-end adjoining relationship.

The left fastener retaining portion 16 extends outwardly from the bridge member left end 30. The right fastener retaining portion 18 extends outwardly from the bridge member right end 32. Each of the fastener retaining portions 16, 18 define a passageway 46 therethrough adapted to receive therein a fastener, such as a screw. The fastener retaining portions 16, 18 and the passageways 46 are adapted to guide a fastener in a direction substantially parallel to the legs 14. Also, the fastener retaining portions 16, 18 each include front and back sides 49 and 51 and are proportioned so that when two of the staples 10 are in end-to-end abutting relation, as shown in FIG. 6, then the fastener retaining portions 16, 18 extending from abutting ends are in side-to-side adjoining relation to each other. In other words, the left fastener retaining portion 16 on one staple 10 lies alongside the right fastener retaining portion 18 of the other staple 10. Moreover, the back side 51 of the left fastener retaining portion 16 of a first staple 10 is positioned in proximity to and facing the front side 49 of the right fastener retaining portion 18 of an adjacent second staple 10.

Figure 4:
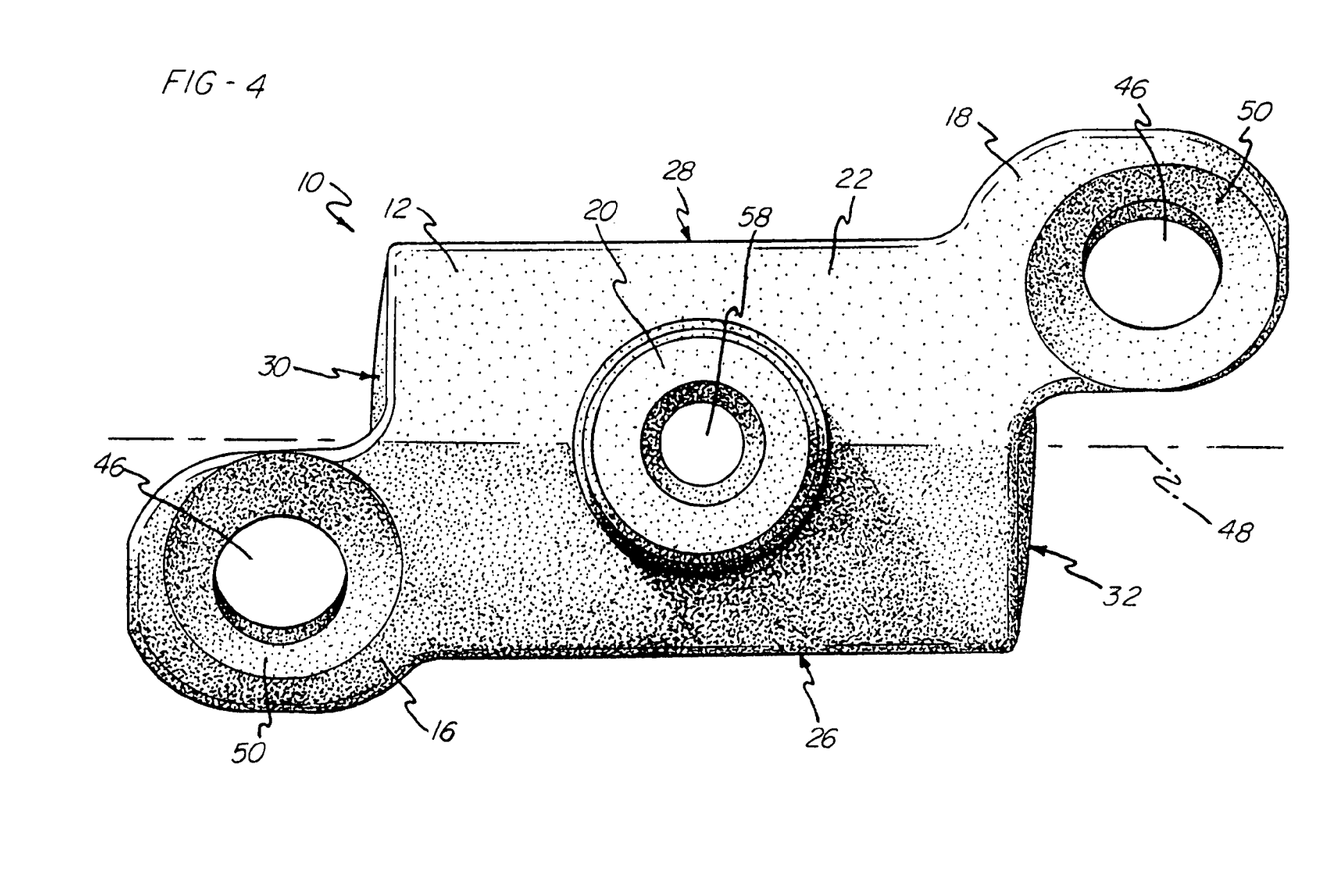
FIG. 4 is a top plan view of the spinal staple.
Figure 5:
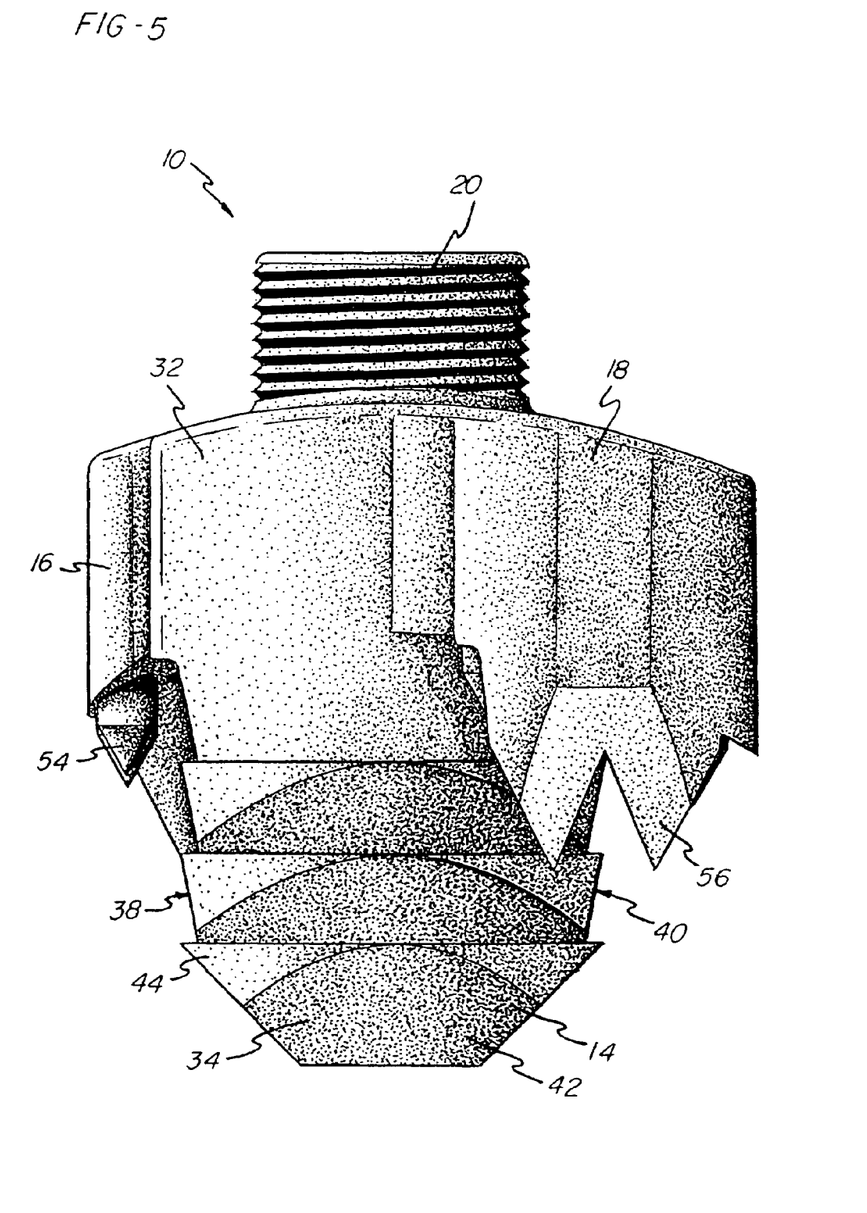
FIG. 5 is an end elevation view of the spinal staple.

As may be seen in FIG. 4, a longitudinal axis 48 extends through the center of the staple 10 from the left end 30 to the right end 32. In a preferred embodiment, the left and right fastener retaining portions 16, 18 lie on opposite sides of the longitudinal axis 48.

Figure 9:
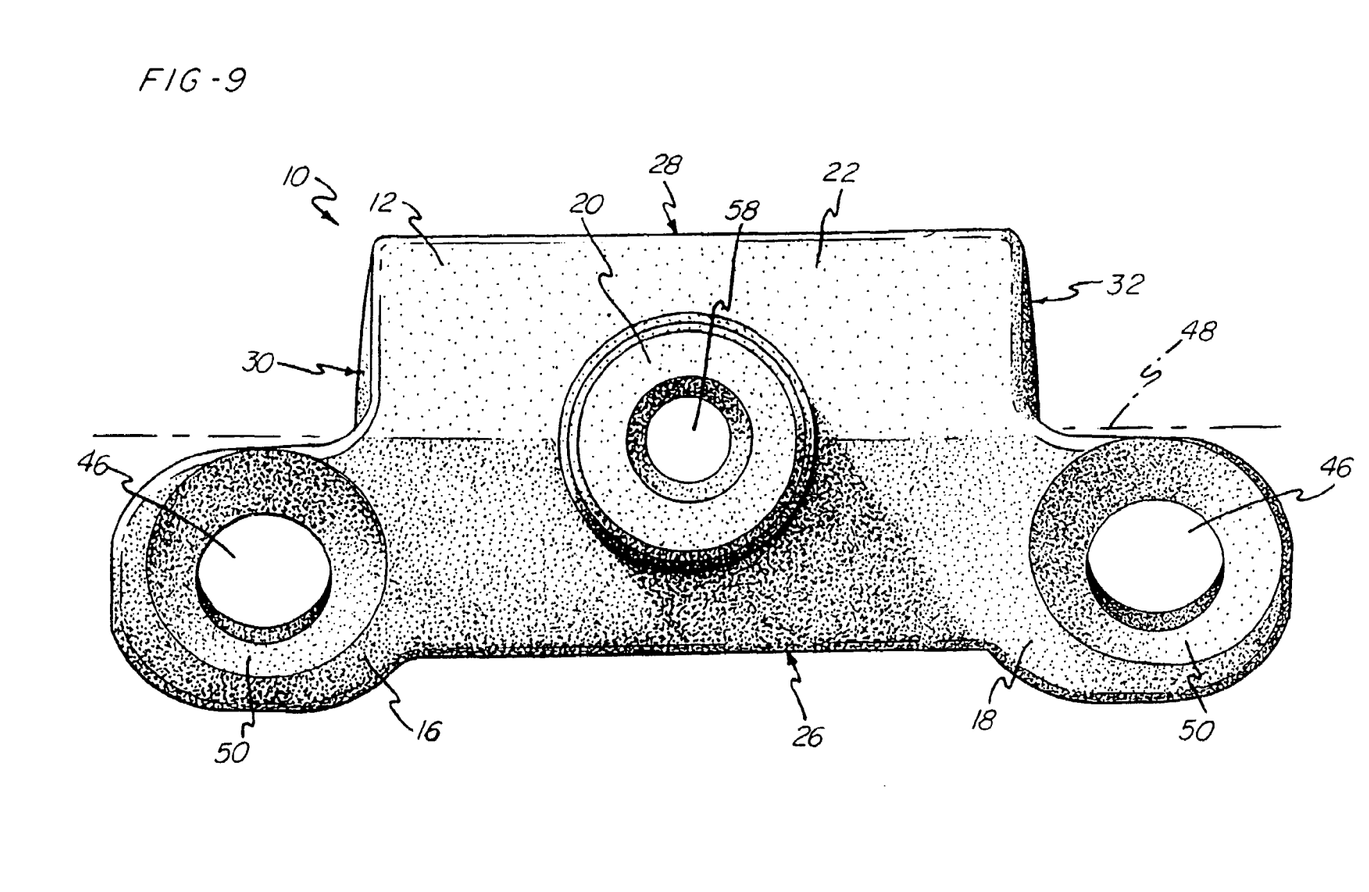
FIG. 9 is a top plan view of an alternative embodiment of the spinal staple in accordance with the invention.
Figure 10:
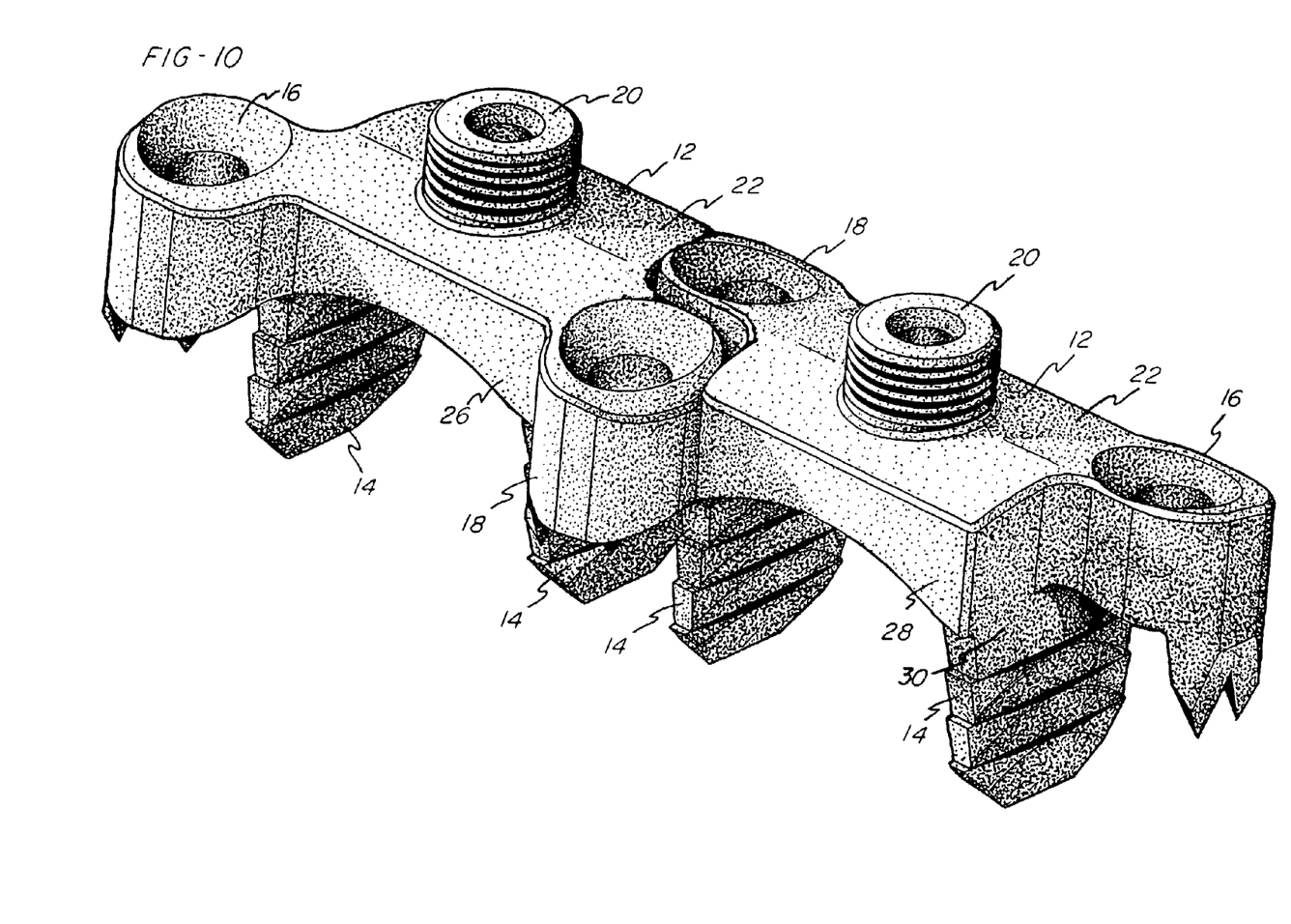
FIG. 10 is a perspective view of two of the alternative embodiment spinal staples aligned in end-to-end adjoining relationship.

In an alternative embodiment, shown in FIGS. 9 and 10, the fastener retaining portions 16 and 18 may extend from opposite ends of the bridge member 12 such that both portions 16 and 18 lie to the same side of the longitudinal axis 48. In such an alternative embodiment, the staples 10 may be arranged in end-to-end abutting relation by rotating adjoining staples end-for-end 180°. Then, the left (right) fastener retaining portion 16 (18) of one staple 10 will lie alongside the left (right) fastener retaining portion 16 (18) of the adjoining staple 10. Moreover, the back side 51 of one fastener retaining portion 16, 18 will be in proximity to and facing the back side 51 of a second fastener retaining portion 16, 18.

Each of the fastener retaining portions 16 and 18 includes a recess, illustratively a counter sunk portion 50, adapted to receive the head of a fastener therein. In addition, each fastener retaining portion 16, 18 also includes a lower surface 52 having a plurality of first pointed projections 54 extending downwardly therefrom for engaging underlying bone. Second pointed projections, or barbs 56, also extend downwardly from the fastener retaining portions 16, 18.

As shown in FIG. 2, the pointed barbs 56 have a length greater than the pointed projections 54 and are positioned at outer extremities of the retaining portions 16 and 18 to resist rotational movement of the staple 10 about its center axis.

The threaded post 20 extends upwardly from the upper surface 22 of the bridge member 12. The threaded post 20 cooperates with the bridge member 12 to define a passageway 58 coaxial with the post 20 and extending through the post 20 to the lower surface 24 of the bridge member 12. The threaded post 20 permits the attachment of additional hardware or instruments to the staple 10, while the passageway 58 allows for the passage of a guide wire for movement therealong, if desired. Further, the cannulated threaded post 20 facilitates attachment of a threaded removable, cannulated impaction device.

The staple 10 may be made of titanium, surgical stainless steel, or any other material sufficiently strong to resist the growth of a spinal column, and sufficiently non-reactive in the environment of a living animal.

Figure 7:
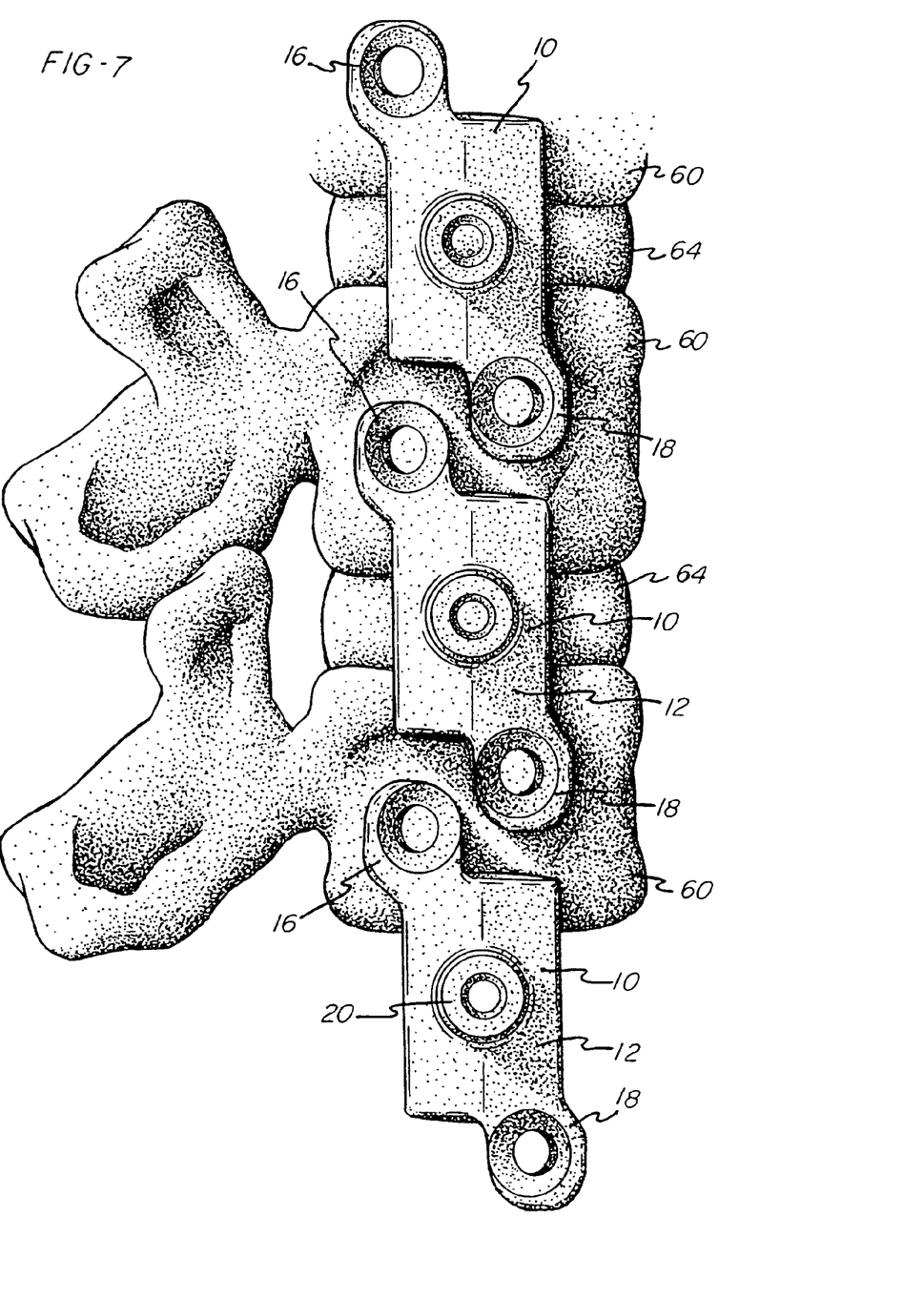
FIG. 7 is a top plan view of three of the spinal staples of the invention installed in a spine in end-to-end relationship.
Figure 8:
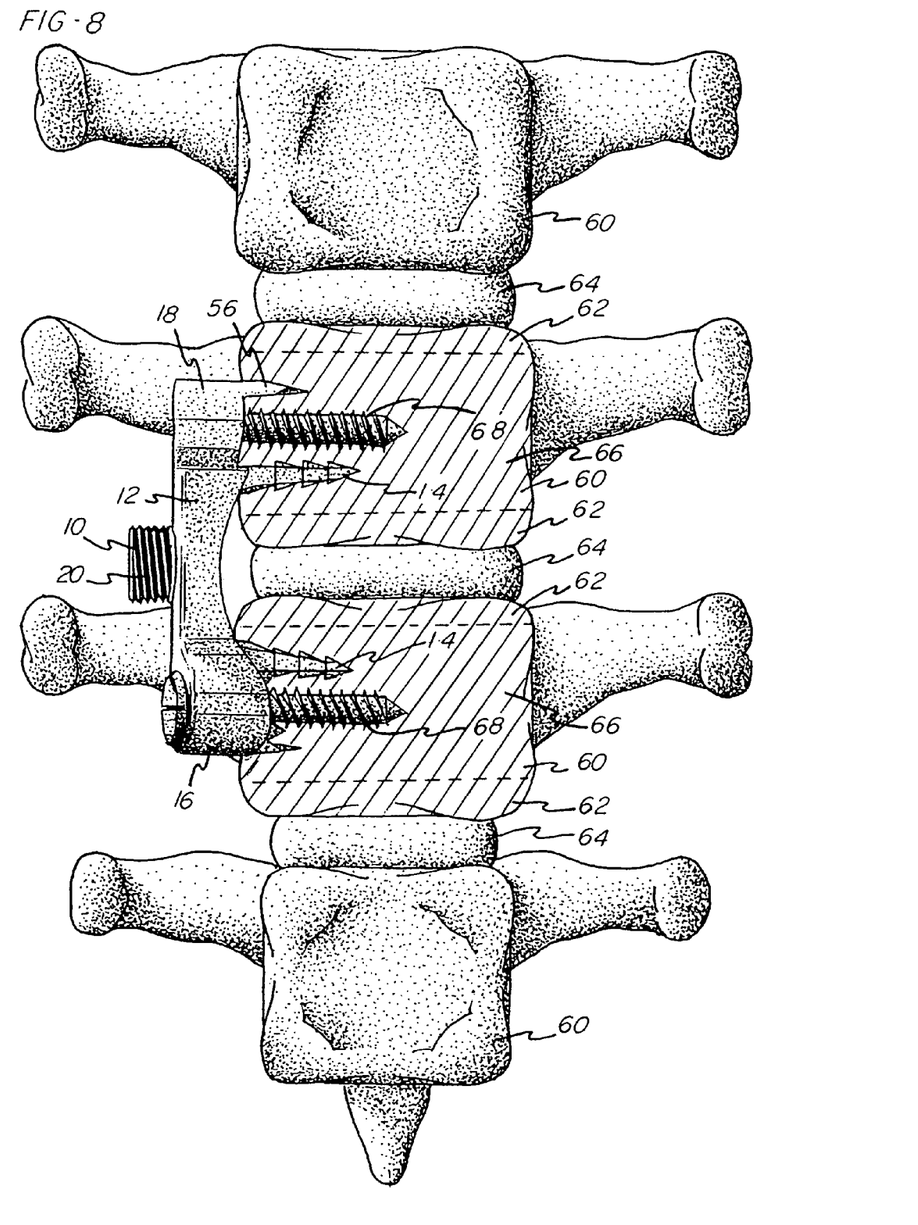
FIG. 8 is an elevation view in partial section of a spinal correction system in accordance with the invention affixed to two vertebrae so as to span two endplate growth centers and an intervening disk.

Referring to FIGS. 7 and 8, the staples 10 are inserted into the vertebrae 60 of an animal having an immature or growing spine exhibiting scoliosis or other spinal deformity. The staples 10 are of a size such that the legs 14 are spaced far enough apart that the staples 10 will bridge longitudinally or lengthwise aligned, adjoining vertebrae 60 having confronting endplate growth centers 62 with predetermined thicknesses, and an intervening disk 64 therebetween. The staples 10 are driven into an intermediate portion 66, between endplate growth centers 62, of adjoining vertebrae 60 on the convex side of the curved spine. The legs 14 are of such a length that they extend into the vertabrae 60 no more than one-half the transverse diameter of each vertebra. When positioned properly, the legs 14 are fully embedded in the vertebrae 60, and the projections 54 and barbs 56 of the fastener retaining portions 16, 18 engage the vertebral surfaces. Once a staple 10 is in place, fasteners 68 such as screws including threaded portions, barbed stakes, or the like are inserted through the passageways 46 in the fastener retaining portions 16, 18 and into the vertebrae 60.

The spinal correction system, when installed on a growing spine having abnormal curvature defining a convex side and an opposed concave side, with the spine including a plurality of lengthwise adjoining vertebrae 60 each having a pair of endplate growth centers 62, or longitudinal growth plates, with an intermediate portion 66 in between, the vertebrae 60 also having a particular diameter or thickness in a direction measured from the convex side to the concave side, is broadly seen to include a first bone engaging means or leg 14 that penetrates the convex side of an intermediate portion 66 of a first vertebra to a depth of less than one-half the diameter of the first vertebra, a second bone engaging means or leg 14 penetrating the convex side of an intermediate portion 66 of a second vertebra to a depth of less than one-half the diameter of the second vertebra, and a bridge member 12 connecting, illustratively rigidly, the first and second bone engaging means 14. As may be appreciated, the concave lower surface 24 of each staple 10 substantially matches or follows the contour of the vertebral body defined by the vertebrae 60.

The spinal correction system 10 thus corrects the abnormal curvature of the growing spine by inhibiting or retarding the growth of the endplate growth centers 62 captured between the first and second bone engaging means 14 on the convex side of the spine, while permitting the unrestrained growth of the endplate growth centers 62 on the concave side of the spine. As the spine continues to grow, the concave side of the spine will grow faster relative to the convex side, thereby resulting in flattening of the curvature and straightening of the spine.

While the legs 14 are primarily responsible for restraining the growth of the endplate growth centers 62 captured therebetween, it will be seen that the fastener retaining portions 16, 18 and fasteners 68 also contribute to restraining the growth of the endplate growth centers 62 captured therebetween. The legs 14 may even be omitted provided that the fastener retaining portions 16, 18 and cooperating fasteners 68 are adapted to sufficiently resist the spreading forces due to lengthwise growth of the endplate growth centers 62.

While the spinal correction system is intended primarily for correcting abnormal lateral curvature of an immature or growing spine, it may also be used for spinal correction in humans having mature or non-growing spines. In such cases, discectomy and fusion would be required before fixing the system to the vertebrae.

While the forms of apparatus herein described constitute preferred embodiments of this invention, it is to be understood that the invention is not limited to these precise forms of apparatus, and that changes may be made therein without departing from the scope of the invention which is defined in the appended claims.

The invention claimed is:

1. A spinal correction system comprising:
   a bridge member having an upper surface, an opposed lower surface, a front side, an opposed back side, a left end, and an opposed right end, said bridge member defining a central longitudinal axis extending between said left end and said right end;
   a left fastener retaining portion extending from said bridge member left end and being laterally offset relative to said longitudinal axis, said left fastener retaining portion having an upper surface, a lower surface, a front side, and a back side;
   a right fastener retaining portion extending from said bridge member right end and being laterally offset relative to said longitudinal axis, said right fastener retaining portion having an upper surface, a lower surface, a front side, and a back side;
   a left leg extending downwardly from said bridge member lower surface proximate said left end of said bridge member and inwardly from said left fastener retaining portion, said left leg including a tapered distal free end defining a blade edge for insertion into bone;
   a right leg extending downwardly from said bridge member lower surface proximate said right end of said bridge member and inwardly from said right fastener retaining portion, said right leg including a tapered distal free end defining a blade edge for insertion into bone, said distal free ends of said right leg and said left leg being positioned in longitudinally spaced relation; and
   wherein each of said fastener retaining portions are proportioned so that when one of said left and right ends of a first spinal correction system is positioned adjacent one of said right and left ends of a second spinal correction system, with the longitudinal axis of the first spinal correction system being substantially aligned with the longitudinal axis of the second spinal correction system, thereby defining a pair of adjacent ends, each of said fastener retaining portions extending from said adjacent ends is positioned asymmetrical to said longitudinal axis with one of said sides facing one of said sides of the other said fastener retaining portion extending from the other said adjacent end.

2. A spinal correction system according to claim 1 wherein:
   said left fastener retaining portion extends from said bridge member left end adjacent one of said bridge member front side and said bridge member back side; and
   said right fastener retaining portion extends from said bridge member right end adjacent the opposite said bridge member side as said left fastener retaining portion.

3. A spinal correction system according to, claim 1 wherein:
said left fastener retaining portion extends from said bridge member left end adjacent one of said bridge member front side and said bridge member back side; and
said right fastener retaining portion extends from said bridge member right end adjacent the same said bridge member side as said left fastener retaining portion.

4. A spinal correction system according to claim 1 wherein:
each said fastener retaining portion defines a passageway therethrough adapted to receive a fastener.

5. A spinal correction system according to claim 1 wherein:
each said fastener retaining portion has a plurality of projections extending from a lower surface thereof.

6. A spinal correction system according to claim 1 wherein:
said bridge member lower surface is concave in a direction from said left end to said right end to substantially match the contour of a vertebral body.

7. A spinal correction system according to claim 1 wherein:
said bridge member lower surface is concave in a direction from said front side to said back side to closely match the contour of a vertebral body.

8. A spinal correction system according to claim 1 wherein:
said left fastener retaining portion lies entirely to one side of said central longitudinal axis;
said right fastener retaining portion lies entirely to the other side of said central longitudinal axis;
each of said fastener retaining portions defines a passageway extending from said upper surface thereof through said lower surface thereof, said passageway adapted to receive a fastener therein; and
each of said fastener retaining portions defines a recess coaxial with said passageway adjacent said fastener retaining portion upper surface, said recess adapted to receive a fastener head therein.

9. A spinal correction system according to claim 1 wherein;
each of said legs includes at least one barb having at least one retaining surface adapted to inhibit withdrawal movement of said spinal correction system once said spinal correction system has been positioned in a fixation environment.

10. A spinal correction system according to claim 1 wherein:
each said leg has a width substantially equal to a width of said bridge member as measured from said front side to said back side.

11. A spinal correction system according to claim 1 wherein:
each said leg includes an inner surface which is splayed outwardly away from said inner surface of the other said leg as measured from a plane passing between said legs substantially perpendicular to said bridge member.

12. A spinal correction system according to claim 1 wherein:
said left fastener retaining portion extends from said bridge member left end adjacent said bridge member front side;
said right fastener retaining portion extends from said bridge member right end adjacent said bridge member back side; and
each of said fastener retaining portions are adapted to guide a fastener in a direction substantially parallel to said legs.

13. A spinal correction system for a spine including longitudinally aligned vertebrae, the vertebrae having confronting endplate growth centers with predetermined thicknesses, a longitudinally extending span defined between the confronting endplate growth center thicknesses, and an intervening disk positioned intermediate the endplate growth centers, the vertebrae having predetermined transverse diameters, said system comprising:
a bridge member having an upper surface, an opposed lower surface, a front side, an opposed back side, a left end, and an opposed right end, the length of said bridge member from said left end to said right end being substantially equal to the longitudinally extending span, said lower surface of said bridge member extending upwardly intermediate said left end and said right end and positioned in spaced relation to, and uncoupled from, the longitudinally extending span;
a left fastener retaining portion extending from said bridge member left end, said left fastener retaining portion having front and back sides;
a right fastener retaining portion extending from said bridge member right end, said right fastener retaining portion having front and back sides;
a left leg extending downwardly from said bridge member lower surface proximate said left end of said bridge member and inwardly from said left fastener retaining portion, said left leg including a tapered distal free end defining a blade edge for insertion into a first vertebra; and
a right leg extending downwardly from said bridge member lower surface proximate said right end of said bridge member and inwardly from said right fastener retaining portion, said right leg including a tapered distal free end defining a blade edge for insertion into a second vertebra, said distal free end of said right leg being positioned in longitudinally spaced relation to said distal free end of said left leg.

14. A spinal correction system according to claim 13 wherein:
each of said fastener retaining portions are proportioned so that when one of said left and right ends of a first spinal correction system is positioned adjacent one of said right and left ends of a second spinal correction system thereby defining a pair of adjacent ends, each of said fastener retaining portions extending from said adjacent ends is positioned with one of said sides facing one of said sides of the other said fastener retaining portion extending from the other said adjacent end.

15. A spinal correction system according to claim 13 wherein:
said left fastener retaining portion extends from said bridge member left end adjacent one of said bridge member front side and said bridge member back side; and
said right fastener retaining portion extends from said bridge member right end adjacent the opposite said bridge member side as said left fastener retaining portion.

16. A spinal correction system according to claim 13 wherein:
said left fastener retaining portion extends from said bridge member left end adjacent one of said bridge member front side or said bridge member back side; and
said right fastener retaining portion extends from said bridge member right end adjacent the same said bridge member side as said left fastener retaining portion.

17. A spinal correction system according to claim 13 wherein:
said legs are proportioned to extend less than one-half said diameter of said vertebrae.

18. A spinal staple comprising:
a bridge member having an upper surface, an opposed lower surface, a front side, an opposed back side, a left end, and an opposed right end;
a left fastener retaining portion extending from said bridge member left end and including a lower surface and a passageway configured to receive a fastener;
a right fastener retaining portion extending from said bridge member right end and including a lower surface and a passageway configured to receive a fastener;
a left leg extending downwardly relative to said lower surface of said bridge member proximate said left end and inboard of said left fastener retaining portion said left leg including a tapered tip defining a blade edge for insertion into a first vertebra, said left leg further including an outer surface, an opposed inner surface, a front surface, an opposed back surface, a width measured from said front surface to said back surface, and a thickness measured from said outer surface to said inner surface, said width being substantially greater than said thickness; and
a right leg extending downwardly relative to said lower surface of said bridge member proximate said right end and inboard of said left fastener retaining portion said right leg including a tapered tip defining a blade edge for insertion into a second vertebra, said right leg further including an outer surface, an opposed inner surface, a front surface, and an opposed back surface, a width measured from said front surface to said back surface, and a thickness measured from said outer surface to said inner surface, said width being substantially greater than said thickness.

19. The spinal staple of claim 18, further comprising a passageway extending through said bridge member from the upper surface to the lower surface, the passageway configured to receive a guidewire for guiding movement of the bridge member along the guidewire.

20. The spinal staple of claim 19, further comprising an attachment member coupled to said bridge member and configured to facilitate attachment of a removable cannulated impact device, said passageway extending through said attachment member.

21. The spinal staple of claim 20, wherein said attachment member includes a post extending upwardly from said bridge member upper surface.

22. The spinal staple of claim 18, said inner surface of each said left leg and said right leg is splayed outwardly away from said inner surface of the other of said right leg and said left leg as measured from a plane passing between said left leg and said right leg substantially perpendicular to said bridge member.

23. The spinal staple of claim 18, further comprising:
at least one projection extending downwardly from said lower surface of said left fastener retaining portion; and
at least one projection extending downwardly from said lower surface of said right fastener retaining portion.

24. A spinal staple comprising:
a bridge member having an upper surface, an opposed lower surface, a front side, an opposed back side, a left end, and an opposed right end;
a left fastener retaining portion extending from said bridge member left end and including a lower surface and a passageway;
a left fastener extending within said passageway of said left fastener retaining portion and configured to be inserted into a first vertebra;
a left leg extending downwardly from the lower surface of the bridge member proximate the left end and inboard of the left fastener retaining portion for insertion into a first vertebra;
a right fastener retaining portion extending from said bridge member right end and including a lower surface and a passageway;
a right fastener extending within said passageway of said right fastener retaining portion and configured to be inserted into a second vertebra;
a right leg extending downwardly from the lower surface of the bridge member proximate the right end and inboard of the right fastener retaining portion for insertion into a second vertebra;
a plurality of first projections each having a first length and extending downwardly from one of said left fastener retaining portion and said right fastener retaining portion; and
a plurality of second projections each having a second length and extending downwardly from one of said lower surface of said left fastener retaining portion and said right fastener retaining portion, each of said second projections being positioned further from said bridge member than each of said first projections, and said second length being greater than said first length.

25. A spinal staple comprising:
a bridge member having an upper surface, an opposed lower surface, a front side, an opposed back side, a left end, and an opposed right end, said bridge member defining a longitudinal axis extending from said left end to said right end;
a left fastener retaining portion extending from said bridge member left end;
a left fastener extending within said left fastener retaining portion and configured to be inserted into a first vertebra;
a right fastener retaining portion extending from said bridge member right end;
a right fastener extending within said right fastener retaining portion and configured to be inserted into a second vertebra;
a left leg extending from said lower surface of said bridge member proximate said left end and inboard of said left fastener retaining portion for insertion into the first vertebra, said left leg including an outer surface, an opposed inner surface, a front surface, and an opposed back surface, said inner surface angled relative to said outer surface and extending from proximate said front side to proximate said back side of said bridge member such that said left leg and said bridge member have substantially equal widths; and
a right leg extending from said lower surface of said bridge member proximate said right end and configured to be inserted into the second vertebra, said left leg including an outer surface, an opposed inner surface, a front surface, and an opposed back surface, said inner surface angled relative to said outer surface and extending from proximate said front side to proximate said back side of said bridge member such that said right leg and said bridge member have substantially equal widths.

26. The spinal staple of claim 25, further comprising a passageway extending through said bridge member from the upper surface to the lower surface, the passageway configured to receive a guidewire for guiding movement of the bridge member along the guidewire.

27. The spinal staple of claim 26, further comprising an attachment member coupled to said bridge member and configured to facilitate attachment of a removable cannulated impact device, said passageway extending through said attachment member.

28. The spinal staple of claim 27, wherein said attachment member includes a post extending upwardly from said bridge member upper surface.

29. The spinal staple of claim 25, wherein each of said left leg and said right leg includes a width measured from said front surface to said back surface, and a thickness measured from said outer surface to said inner surface, said width being substantially greater than said thickness.

30. The spinal staple of claim 25, wherein said inner surface of each said left leg and said right leg is splayed outwardly away from said inner surface of the other of said right leg and said left leg as measured from a plane passing between said left leg and said right leg substantially perpendicular to said bridge member.

31. The spinal staple of claim 30, wherein said outer surface of each said left leg and said right leg extends substantially perpendicular to said bridge member.

32. The spinal staple of claim 25, wherein the left fastener retaining portion and the right fastener retaining portion are laterally offset relative to said longitudinal axis.

* * * * *